United States Patent
Biedermann et al.

(10) Patent No.: US 11,197,693 B2
(45) Date of Patent: Dec. 14, 2021

(54) RECEIVING PART FOR COUPLING A BONE ANCHOR TO A ROD AND BONE ANCHORING DEVICE WITH SUCH A RECEIVING PART

(71) Applicant: BIEDERMANN TECHNOLOGIES GMBH & CO. KG, Donaueschingen (DE)

(72) Inventors: Lutz Biedermann, Villingen (DE); Bernd Fischer, Bräunlingen (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 0 days.

(21) Appl. No.: 16/796,336

(22) Filed: Feb. 20, 2020

(65) Prior Publication Data
US 2020/0261118 A1    Aug. 20, 2020

Related U.S. Application Data

(63) Continuation of application No. 15/823,082, filed on Nov. 27, 2017, now Pat. No. 10,610,260, which is a
(Continued)

(30) Foreign Application Priority Data

Nov. 20, 2014    (EP) ..................................... 14194064

(51) Int. Cl.
*A61B 17/70*    (2006.01)
*A61B 17/86*    (2006.01)

(52) U.S. Cl.
CPC ...... *A61B 17/7002* (2013.01); *A61B 17/7032* (2013.01); *A61B 17/7037* (2013.01); *A61B 17/8605* (2013.01)

(58) Field of Classification Search
None
See application file for complete search history.

(56) References Cited

U.S. PATENT DOCUMENTS 6,254,602 B1 *  7/2001  Justis ................. A61B 17/7032
                                                   606/272
6,547,789 B1    4/2003  Ventre et al.
(Continued)

FOREIGN PATENT DOCUMENTS

CN      103687560 A      3/2014
FR      2 904 526 A1     2/2008
(Continued)

OTHER PUBLICATIONS

Extended European Search Report issued by the EPO for EP 14194064.3 dated May 8, 2015 (7 pages).

*Primary Examiner* — Tessa M Matthews
(74) *Attorney, Agent, or Firm* — Lewis Roca Rothgerber Christie LLP

(57) ABSTRACT

A receiving part for coupling a bone anchor to a rod is provided, where the bone anchor includes a shank for anchoring to a bone or a vertebra. The receiving part includes a first end and a second end, the second end being connected to the shank, a bore extending from the first end into the receiving part for receiving a fixation device, the bore having a bore axis, and a recess for receiving a rod, the recess being open at the first end of the receiving part for allowing insertion of the rod and having opposing sidewalls on at least one side of the bore. When a rod is inserted into the recess, a longitudinal axis of the rod extends substantially perpendicular to the bore axis. A resilient retention element is provided on at least one of the opposing sidewalls, where the resilient retention element is deflectable toward the at least one sidewall when the rod is inserted.

20 Claims, 10 Drawing Sheets

Related U.S. Application Data continuation of application No. 14/946,583, filed on Nov. 19, 2015, now Pat. No. 9,861,388.

(60) Provisional application No. 62/082,517, filed on Nov. 20, 2014.

(56) References Cited

U.S. PATENT DOCUMENTS

| | | | |
|---|---|---|---|
| 7,731,736 | B2 | 6/2010 | Guenther et al. |
| 8,444,682 | B2 * | 5/2013 | Yeung ................ A61B 17/7032 606/305 |
| 8,465,528 | B2 | 6/2013 | Schumacher |
| 8,506,609 | B2 | 8/2013 | Biedermann et al. |
| 8,512,382 | B2 | 8/2013 | Cawley et al. |
| 8,663,298 | B2 | 3/2014 | Keyer et al. |
| 8,974,507 | B2 | 3/2015 | Eisermann |
| 9,034,022 | B2 | 5/2015 | Assad et al. |
| 9,254,150 | B2 | 2/2016 | Biedermann et al. |
| 9,282,998 | B2 | 3/2016 | Schlaepfer et al. |
| 9,320,546 | B2 | 4/2016 | Keyer et al. |
| 9,326,796 | B2 | 5/2016 | Harvey et al. |
| 9,387,013 | B1 * | 7/2016 | Shoshtaev .......... A61B 17/7056 |
| 9,439,681 | B2 | 9/2016 | Keyer et al. |
| 9,510,868 | B2 | 12/2016 | Biedermann et al. |
| 2005/0277927 | A1 * | 12/2005 | Guenther ........... A61B 17/7032 606/308 |
| 2006/0293664 | A1 | 12/2006 | Schumacher |
| 2007/0233079 | A1 | 10/2007 | Fallin et al. |
| 2007/0270810 | A1 * | 11/2007 | Sanders ............. A61B 17/7041 606/264 |
| 2009/0062860 | A1 | 3/2009 | Frasier et al. |
| 2009/0088809 | A1 | 4/2009 | Fisher et al. |
| 2010/0168800 | A1 | 7/2010 | Biedermann et al. |
| 2010/0204735 | A1 | 8/2010 | Gephart et al. |
| 2012/0165874 | A1 | 6/2012 | Biedermann et al. |
| 2013/0123858 | A1 | 5/2013 | Attia |
| 2013/0345756 | A1 | 12/2013 | Berrevoets et al. |
| 2014/0121703 | A1 | 5/2014 | Jackson et al. |
| 2014/0214097 | A1 | 7/2014 | Jackson et al. |
| 2014/0303675 | A1 | 10/2014 | Mishra |
| 2014/0330315 | A1 | 11/2014 | Butler et al. |
| 2019/0029729 | A1 | 1/2019 | Mire et al. |

FOREIGN PATENT DOCUMENTS

| | | |
|---|---|---|
| JP | 2001-017441 A | 1/2001 |
| JP | 2008-502458 A | 1/2008 |
| JP | 2012-130696 A | 7/2012 |
| JP | 2014-527851 A | 10/2014 |
| WO | WO 2013/012763 A1 | 1/2013 |

* cited by examiner

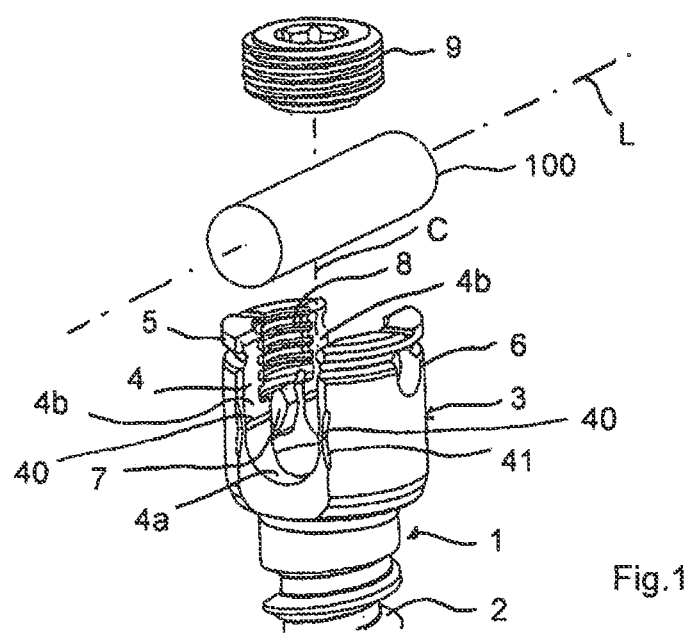
Fig. 1
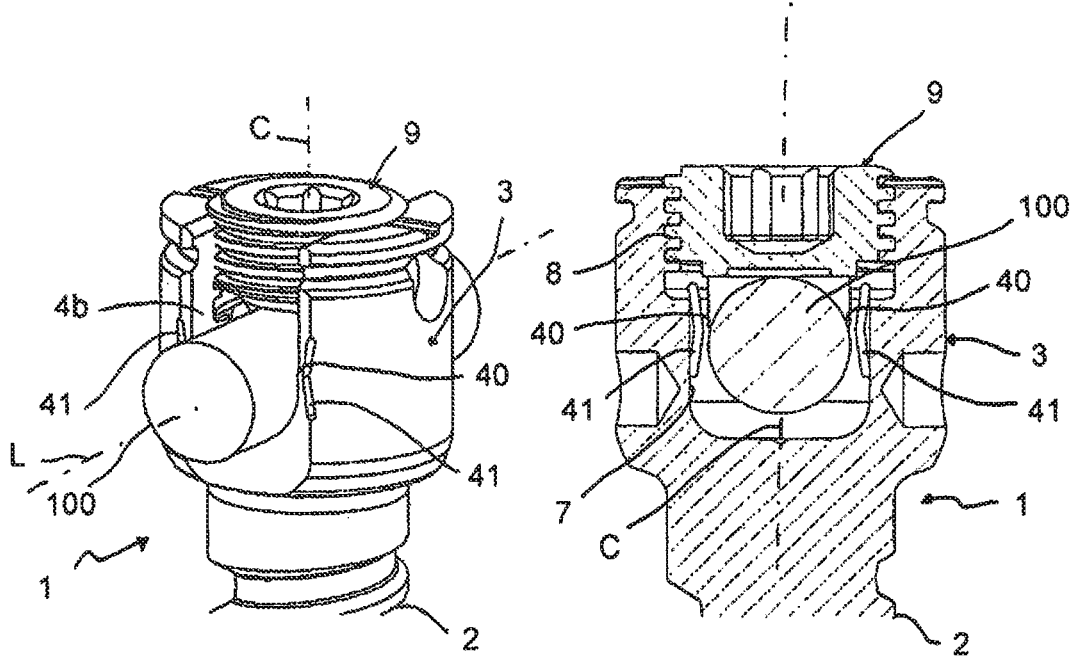
Fig. 2
Fig. 3

RECEIVING PART FOR COUPLING A BONE ANCHOR TO A ROD AND BONE ANCHORING DEVICE WITH SUCH A RECEIVING PART

CROSS-REFERENCE TO RELATED APPLICATIONS

The present application is a continuation of U.S. patent application Ser. No. 15/823,082, filed Nov. 27, 2017, which is a continuation of U.S. patent application Ser. No. 14/946,583, filed Nov. 19, 2015, now U.S. Pat. No. 9,861,388, which claims the benefit of U.S. Provisional Application Ser. No. 62/082,517, filed Nov. 20, 2014, the contents of which are hereby incorporated by reference in their entirety, and claims priority to European Patent Application EP 14 194 064.3, filed Nov. 20, 2014, the contents of which are hereby incorporated by reference in their entirety.

BACKGROUND

Field

The present disclosure relates to a receiving part for coupling a bone anchor to a rod and to a bone anchoring device including such a receiving part. More specifically, the present disclosure relates to a receiving part having a recess for receiving a rod therein and at least one resilient retention element for temporarily holding the rod in the recess. The bone anchoring device is particularly suitable for use in spinal stabilization systems.

Description of the Related Art

The process of stabilizing a spinal column using a spinal stabilization system involves the placement of bone anchors, for example pedicle screws, and a rod connecting the bone anchors. During the surgical procedure, the receiving parts of the bone anchors have to be aligned so that the rod can be inserted and finally fixed. It may happen that a rod, once inserted in one of the receiving parts, slips out before it is fixed. This can render the surgical procedure difficult and time consuming, and is therefore not desirable.

From U.S. Pat. No. 7,731,736 B2, a receiver of a bone fixation system is known that automatically provisionally retains a rod when the rod is inserted into the receiver. The receiver includes a rod seat and spaced apart legs that include provisional retention structures in the form of opposing tabs. The tabs project laterally into a pocket of the receiver. Prior to insertion of the rod into the receiver, the legs of the receiver are in a non-deflected orientation. As the rod is pressed downwardly in the pocket, the rod causes the legs to deflect apart to accommodate the rod. In certain embodiments, the partially deflected legs apply a clamping force to the rod.

SUMMARY

Embodiments of the invention provide an improved receiving part for coupling a rod to a bone anchor. Embodiments also provide a bone anchoring device including such a receiving part that allows temporarily holding the rod and that is applicable to various types of receiving parts independent of their specific design.

According to embodiments of the present invention, a receiving part for coupling a bone anchor to a rod is provided that includes a recess for receiving the rod and a bore for inserting a fixation device. A bore axis of the receiving part is substantially perpendicular to a longitudinal axis of the rod to be inserted and the recess has opposing sidewalls and a resilient retention element protruding from at least one of the opposing sidewalls. When the rod is inserted into the recess, the rod can be held temporarily in the recess by the at least one retention element.

Because the retention element is provided on a sidewall of the recess and not within the bore that accommodates the fixation device, any hitherto known design of a receiving part that has a recess for the rod can be provided with such a retention element without substantially changing the design of the receiving part and the design of other parts interacting therewith. The function of the retention element is the same in all types of receiving parts, such as receiving parts of monoaxial bone anchoring devices, receiving parts of polyaxial bone anchoring devices that are of the top-loading type or the bottom-loading type, and receiving parts where the clamping and locking of a head of a bone anchor is achieved by an outer locking ring. After final fixation of the rod with the fixation device, the retention element may have no further function.

The retention element prevents the rod from slipping out of the recess, in particular, from inadvertently slipping-out of the recess during steps of inserting the rod into a plurality of bone anchoring devices or adjustment of the position of a bone anchoring device relative to the rod.

The retention element may be provided at a position in the receiving part such that the retention element exerts a frictional force onto the rod for provisionally holding the rod in a position in the recess.

In a further embodiment, the receiving part with the retention element can be configured such that rods of different diameters can be held. To achieve this, a bottom of the recess that forms a rod seat may have a specific shape, such as a V-groove. Such a configuration allows a single bone anchoring device to be used with rods having different diameters.

In a further embodiment, the retention element may be provided on only one sidewall of the recess. Further, an insertion portion of the recess for inserting the rod may be offset from the bore axis of the receiving part, and the rod seat in the bottom of the channel may be substantially symmetrical to the bore axis. The retention function of the retention element may be enhanced by this configuration.

In a still further embodiment, the retention element is formed by a separate part from the receiving part that is connectable to the sidewall of the recess. Thereby, a material for the retention element can be used that renders the retention element particularly elastic. The material of the retention element may be different from the material of the receiving part.

BRIEF DESCRIPTION OF THE DRAWINGS

Further features and advantages of the present invention will become apparent by the description of embodiments by the means of the accompanying drawings. In the drawings:

FIG. 1 shows an exploded perspective view of one embodiment of a bone anchoring device including a monoaxial bone anchor having a shank (shown only partially) and a receiving part, a rod, and a fixation device;

FIG. 2 shows a perspective view of the bone anchoring device of FIG. 1 in an assembled condition;

FIG. 3 shows a cross-sectional view of the assembled bone anchoring device of FIGS. 1 and 2, the cross-section taken along a plane extending through a bore axis of the receiving part and perpendicular to a longitudinal axis of the rod;

FIG. 22b shows a detail of FIG. 22a;

FIG. 24b shows a detail of FIG. 24a;

DETAILED DESCRIPTION

Figure 4A:
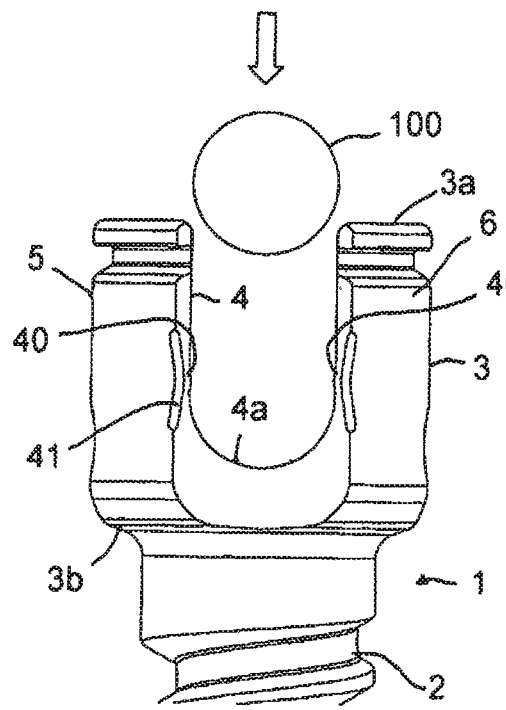
FIGS. 4a to 4d show front views of steps of inserting and holding a rod in the receiving part of the bone anchoring device of FIGS. 1 to 3.

An embodiment of a receiving part is depicted in FIGS. 1 to 3, illustrating a monoaxial bone anchoring device 1. The bone anchoring device 1 has a shank 2 with a bone thread section, a tip (not shown), and a receiving part 3 rigidly connected to the shank 2 for receiving a rod 100 connecting the bone anchoring device 1 to another bone anchoring device 1. The term monoaxial means that the shank axis extends at a fixed angle with respect to the receiving part 3. In the embodiment shown in FIGS. 1 to 3, the angle between the shank axis and the receiving part 3 is zero degrees, but it may be another angle. The receiving part 3 includes a first end 3a and an opposite second end 3b, where the second end 3b is adjacent to the shank 2. At the first end 3a, a channel for the rod 100 in the form of a recess 4 is provided that has a substantially U-shaped cross-section with a bottom 4a of the recess 4 forming a seat for the rod 100. The recess 4 forms two free legs 5, 6. A bore 7 in the receiving part 3 extends from the first end 3a toward the second end 3b and to a depth below the bottom 4a of the recess 4. Adjacent to the first end 3a, an internal thread 8 is provided on the legs 5, 6. The internal thread 8 cooperates with a corresponding external thread of a fixation element or device 9. In the embodiment shown, the fixation element 9 is a set screw. The bore 7 has a bore axis C that is coaxial with the axis of rotation of the threaded shank 2. Opposing sidewalls 4b of the recess 4 are formed on either side of the bore 7, hence, one pair of opposing sidewalls 4b is respectively arranged on each side of the bore 7.

On each of the sidewalls 4b of the recess 4, a retention element 40 is provided that is configured to reduce a width of the substantially U-shaped recess 4 in a direction perpendicular to the bore axis C. The retention elements 40 protrude into the recess 4 such that a distance between two respectively opposing retention elements 40 is smaller than a width of the rod 100. In the case of the cylindrical rod 100 according to the embodiment in FIGS. 1 to 3, the distance between the retention elements 40 of respectively opposing sidewalls 4b is smaller than a diameter of the rod 100. The retention elements 40 have the shape of ribs that extend perpendicular to the bore axis C and parallel to a longitudinal axis L of the rod 100. The retention elements 40 are positioned in an axial direction of the bore axis C at or above a center of the rod 100 measured from the bottom 4a of the recess 4 when the rod 100 is inserted and supported therein.

The retention elements 40 are resilient. In particular, the retention elements 40 of this embodiment are formed as a monolithic piece with each respective sidewall 4*b*. The resiliency of the retention elements 40 is such that when the rod 100 is inserted into the recess 4, the retention elements 40 are configured to move outward, i.e., away from the bore axis C, such that the distance between the retention elements 40 increases so that the rod 100 can pass therethrough. When the rod 100 is removed from the recess 4 and pressure is no longer exerted onto the retention elements 40 by the rod 100, the retention elements 40 return to their original shape, thereby again restricting the width of the recess 4.

The resiliency of the retention elements 40 is achieved by an angled slit or recess 41 in each of the respective sidewalls 4*b*. Each recess 41 completely extends through the respective sidewall 4*b* from an outside of the receiving part 3 and extends into the bore 7 in a direction substantially perpendicular to the bore axis. Hence, the recesses 41 are open at two sides. A cross-section of the recesses 41 resembles a V-shape with an obtuse angle between the legs of the V. Due to the recess 41, the ribs that form the retention elements 40 can be pressed outward to move into the space of the recesses 41.

The size, the shape and the position of the recesses 41 can be selected to obtain a desired flexibility of the retention elements 40.

An outer shape of the receiving part 3 may be substantially cylindrical, but any other shape may be contemplated.

The parts of the bone anchoring device 1 are made of a body-compatible material, for example, a body-compatible metal, a body-compatible metal alloy, or a body-compatible plastic material. Examples of such materials are stainless steel, titanium, nickel titanium alloys NiTi, for example Nitinol, β-titanium and PEEK (polyether ether ketone). In particular, the portion of the bone anchoring device 1 including the retention elements 40 may be made from a material that provides highly elastic properties, such as, for example, super-elastic shape memory alloys such as Nitinol or β-titanium. Additionally, the bone anchoring device 1 or parts thereof can be at least partially made of biodegradable materials. In particular, such materials include degradable polymers, such as, for example, PLLA (poly-L lactide), degradable metals, such as, for example, magnesium, or degradable metal alloys, for example magnesium-based or iron-based alloys.

Figure 4B:
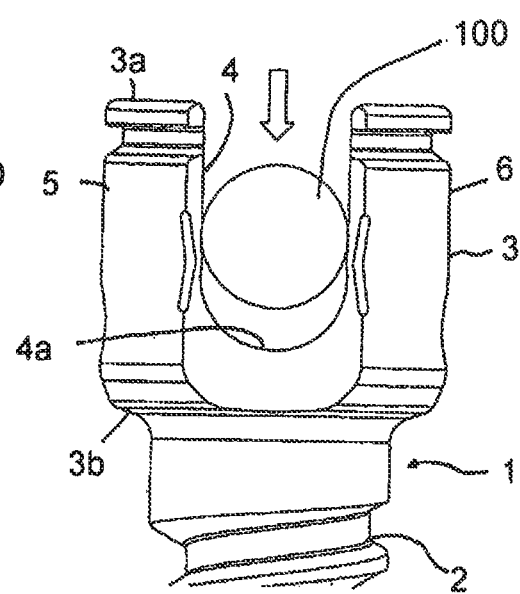
Figure 4C:
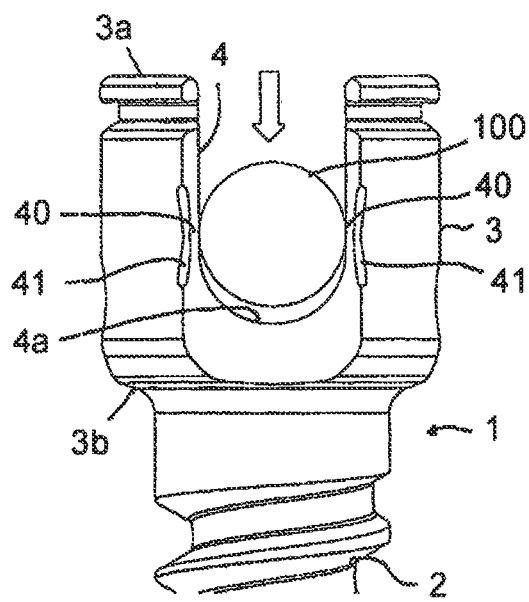
Figure 4D:
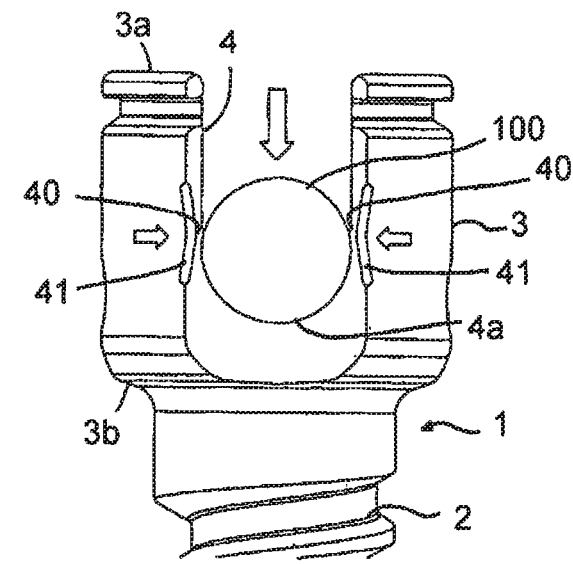

In use, once the shank 2 of the bone anchoring device 1 is anchored to a bone or vertebra, the rod 100 can be inserted into the receiving part 3 and can be held therein as depicted in FIGS. 4*a* to 4*d*. As can be seen in FIG. 4*a*, in their resting position, the retention elements 40 narrow the channel for the rod 100 such that the distance between the innermost surfaces of respectively opposing retention elements 40 is smaller than a diameter of the rod 100. Next, as shown in FIG. 4*b*, when the rod 100 is inserted into the receiving part 3, the rod 100 cannot automatically pass between the retention elements 40. If the rod 100 is pressed downward, the rod 100 exerts a transverse force onto the retention elements 40, as depicted in FIG. 4*c*. The retention elements 40 are deflected outward and the channel is widened to let the rod 100 pass therethrough. Finally, when the rod 100 is seated on the bottom 4*a* of the recess 4, the retention elements 40 tend to return to their original shape due to their resiliency, thereby exerting a transverse frictional force onto the rod 100 that holds the rod 100 provisionally, for example, until final fixation by the fixation device 9. The rod 100 may be held both in the vertical position (i.e., in the rod seat at the bottom 4*a* of the recess 4), and also in the horizontal position (i.e., the rod's 100 position along the length of the channel).

In a non-deflected condition, the position of the ribs is such that the retention elements 40 are at or above an area with the greatest diameter of the rod 100 when the rod 100 is seated in the bottom 4*a* of the recess 4, i.e., at an axial position at or above the radius of the rod 100 as measured from the bottom 4*a* of the recess 4. As such, the rod 100 is prevented from moving out through the first end 3*a* of the receiving part 3 once the rod 100 is seated.

Figure 5:
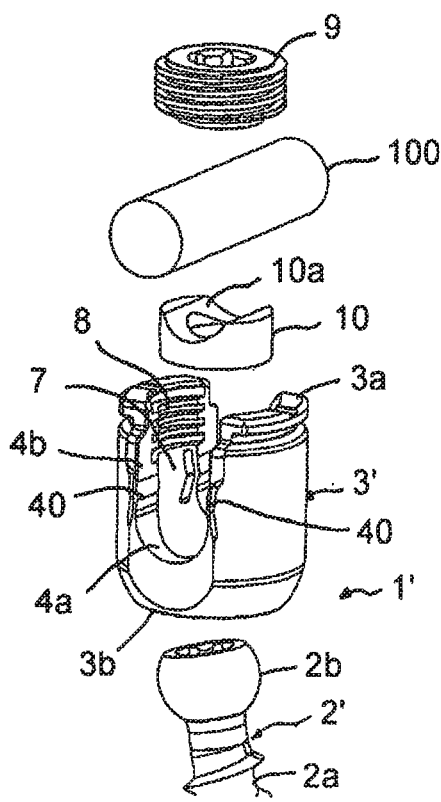
FIG. 5 shows an exploded perspective view of a modified embodiment of the bone anchoring device of FIGS. 1 to 3, including a receiving part, a separate bone anchor that is polyaxially connectable to the receiving part, a rod, and a fixation device.
Figure 6:
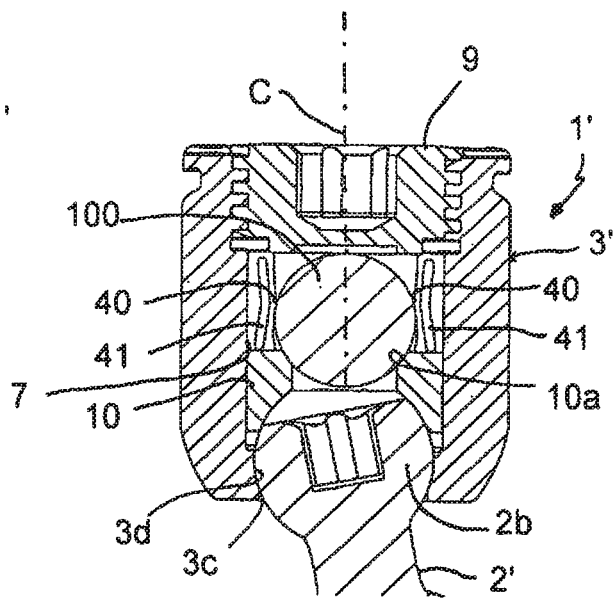
FIG. 6 shows a cross-sectional view of the modified embodiment of the bone anchoring device according to FIG. 5 in an assembled state, the cross-section taken along a plane extending through a bore axis of the receiving part and perpendicular to a longitudinal axis of the rod.

A modified embodiment of a receiving part 3' is explained with reference to FIGS. 5 and 6, depicting a polyaxial bone anchoring device 1'. Parts and portions that are identical or similar to the parts and portions of the previous embodiment are described with the same reference numerals and the detailed description thereof is not repeated. An example polyaxial bone anchoring device 1' includes a bone anchor 2' that has a shank 2*a* and a head 2*b*, which may be a spherical segment-shaped head. A receiving part 3' includes, in addition to the portions of the previous embodiment, an opening 3*c* at the second end 3*b* and a seat 3*d* for the head 2*b* of the bone anchor 2'. The seat 3*d* can be a spherically-shaped seat or any other seat that allows the head 2*b* of the bone anchor 2' to pivot therein. The seat 3*d* is in communication with the bore 7. The example polyaxial bone anchoring device 1' is of the top-loading type, i.e., the bone anchor 2' is inserted into the receiving part 3' from the top or first end 3*a*. A pressure element 10 is provided that is arranged in the bore 7 and that is configured to exert pressure onto the head 2*b* of the bone anchor 2' to lock the head 2*b* in a desired angular orientation with respect to the receiving part 3'. Hence, the term polyaxial means that the shank 2*a* of the bone anchor 2' can assume various angles with respect to the receiving part 3'. Furthermore, the pressure element 10 provides a support surface 10*a* for the rod 100, which forms the rod seat in this embodiment. The retention elements 40 are identical or similar to the retention elements 40 of the previous embodiment. In an assembled state as shown in FIG. 6, when the head 2*b* of the bone anchor 2' is in the seat 3*d*, when the pressure element 10 is on top of the head 2*b*, and when the rod 100 is inserted, the position of the retention elements 40 is such that the ribs are at an axial distance from the rod support surface 10*a* of the pressure element 10 that is equal to or greater than the radius of the rod 100.

Figure 7:
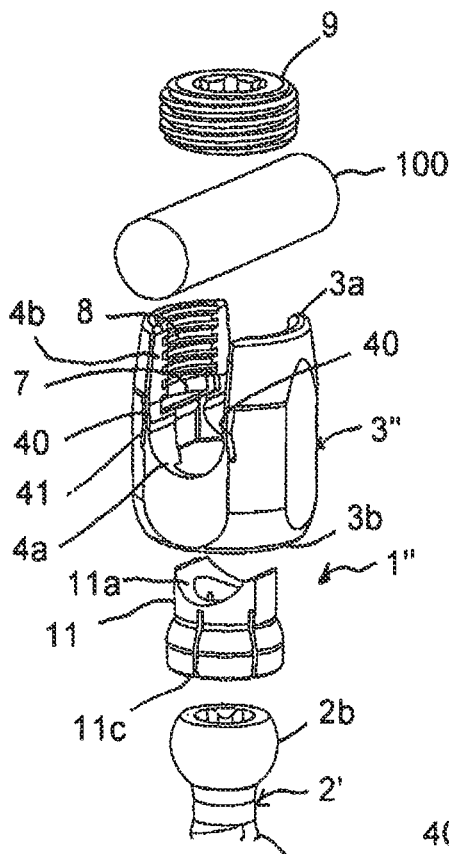
FIG. 7 depicts a further modified embodiment of the bone anchoring device of FIGS. 1 to 3, including a receiving part, a separate bone anchor that is polyaxially connectable to the receiving part, a rod, and a fixation device.
Figure 8:
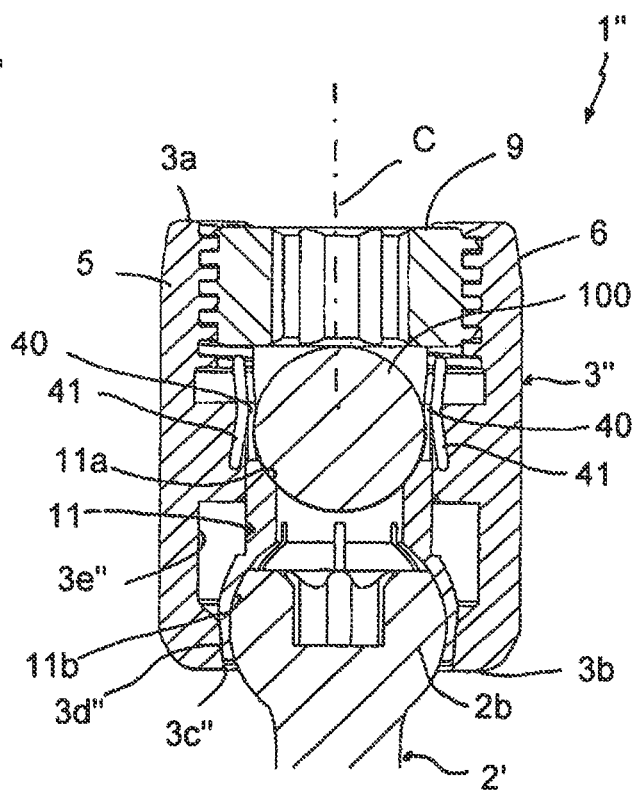
FIG. 8 shows a cross-sectional view of the bone anchoring device of FIG. 7 in an assembled state, the cross-section taken in a plane extending through a bore axis of the receiving part and perpendicular to a longitudinal axis of the rod.

A further modified embodiment will be explained with reference to FIGS. 7 and 8. Parts and portions that are identical or similar to parts and portions of the previous embodiments will be described with the same reference numerals and the description thereof is not repeated. The bone anchoring device 1" shown in FIGS. 7 and 8 is an example polyaxial bone anchoring device of the bottom-loading type. The bone anchoring device 1" includes a separate bone anchor 2' as in the previous embodiment and a receiving part 3". The receiving part 3" includes an opening 3*c"* at the second end 3*b* that is larger than the diameter of the head 2*b* of the bone anchor 2'. Furthermore, the receiving part 3" has an accommodation space 3*e"* that narrows in a narrowing portion 3*d"* towards the lower opening 3*c"*. The accommodation space 3*e"* accommodates the head 2*b* and a cap-like pressure element 11 including a cap-like portion 11*b* that is flexible due to slits 11*c* and extends over the area with the greatest outer diameter of the spherical segment-shaped head 2*b*. Opposite to the cap-like portion 11*b*, the pressure element 11 includes a rod support surface 11*a* for supporting the rod 100, which forms a rod seat in this embodiment. The dimensions of the receiving part 3" and the pressure element 11 are such that when the pressure element 11 is placed in the receiving part 3'", the pressure element 11 can assume an inserting position in which the cap-like portion 11*b* can expand in the accommodation space 3*e*'' to allow insertion of the head 2*b*. Next, the pressure element 11 can assume a pre-locking position in which the pressure element 11 is moved downward when the head 2*b* is inserted therein such that the cap-like portion 11*b* is clamped in the narrowing portion 3*d*'' of the accommodation space 3*e*'' to prevent removal of the inserted head 2*b*. Finally, the pressure element 11 can assume a locking position, in which the pressure element 11 and the inserted head 2*b* are moved downward to such an extent that the head 2*b* is locked by a clamping force exerted by the narrowing portion 3*d*'' onto the cap-like portion 11*b* and the head 2*b*. As in the previous embodiments, the retention elements 40 are provided in the sidewalls 4*b* of the recess 4 of the receiving part 3''. The retention elements 40 are located at such a height that an inserted rod 100 that is placed onto the rod support surface 11*a* is held in this position by the retention elements 40.

Figures 9, 10:
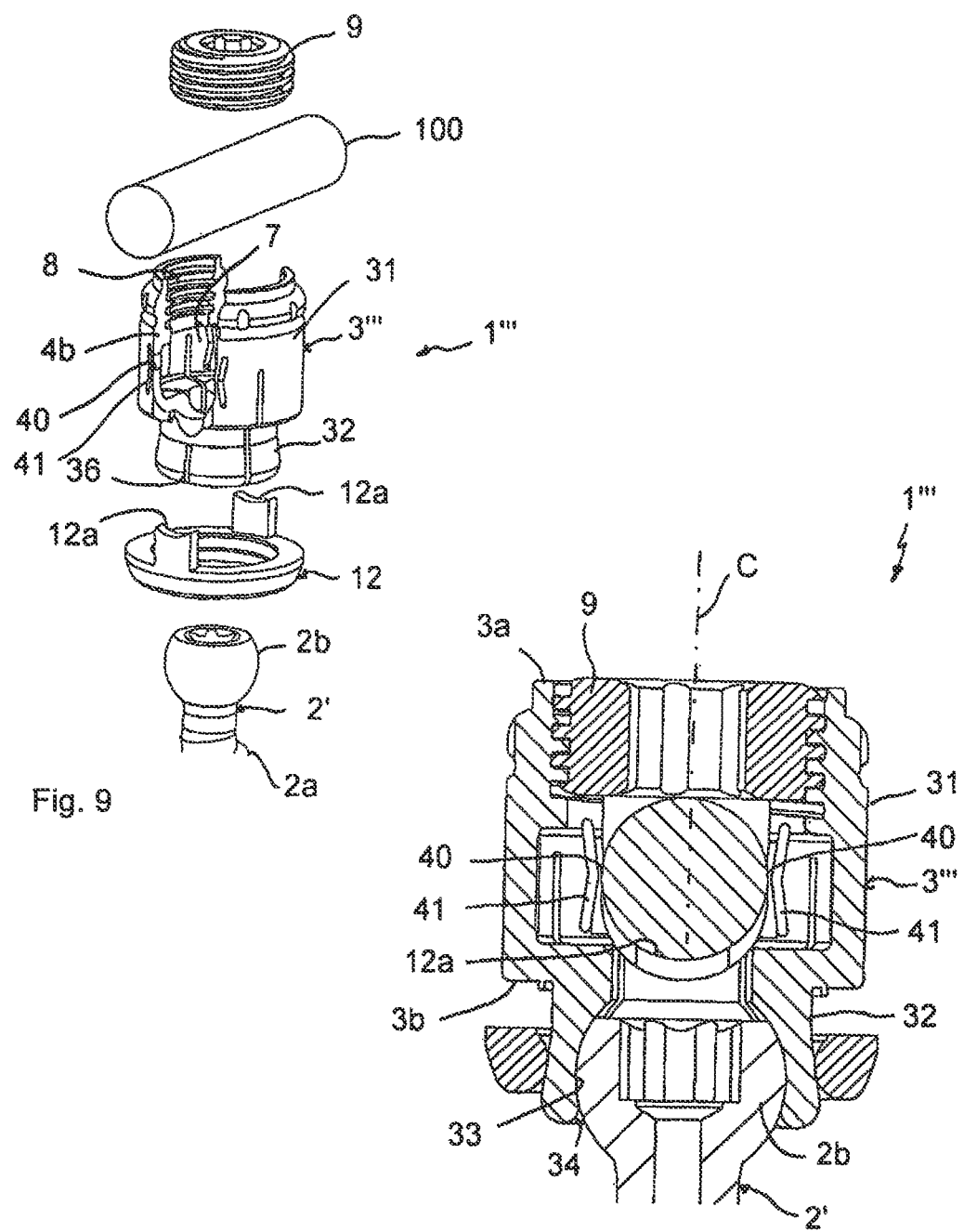
FIG. 9 shows a still further modified embodiment of the bone anchoring device of FIGS. 1 to 3, including a receiving part, a separate bone anchor that is poyaxially connectable to the receiving part and that can be locked by an outer ring, a rod, and a fixation device.
FIG. 10 shows a cross-sectional view of the bone anchoring device shown in FIG. 9 in an assembled state, the cross-section taken in a plane extending through a bore axis of the receiving part and perpendicular to a longitudinal axis of the rod.

A still further modified embodiment will be explained with reference to FIGS. 9 and 10. The bone anchoring device 1''' shown in FIGS. 9 and 10 is a bottom-loading polyaxial bone anchoring device, where the head 2*b* of the bone anchor 2' is clamped by an outer ring. The receiving part 3''' has a rod-receiving portion 31 that includes the recess 4 forming the channel for the rod 100, the retention elements 40, and the bore 7. Adjacent to the rod-receiving portion 31, a head-receiving portion 32 is provided that has a hollow interior 33 with an opening towards the second end 3*b* and a flexible wall that is flexible due to slits 36 that are open to the second end 3*b*. The hollow interior 33 is sized and shaped to accommodate the head 2*b* therein. The head 2*b* may be held in the head-receiving portion 32 by friction. A locking ring 12 is provided that extends around the head-receiving portion 32. Two opposite projections 12*a* on the locking ring 12 may form the rod seat in this embodiment. The locking ring 12 can be moved from a first position closer to the rod-receiving portion 31, which allows insertion of the head 2*b* through the lower opening 34 until the head-receiving portion 32 covers the head 2*b* through pressure with the rod 100. The locking ring 12 can be moved to at least a second position in which the locking ring 12 is closer to the second end 3*b* than in the first position and in which the head 2*b* is prevented from moving out through the lower opening 34. The locking ring 12 may further assume a third position even closer to the second end 3*b* than the second position in which the locking ring 12 compresses the head-receiving portion 32 such that the head 2*b* is locked.

Figure 11:
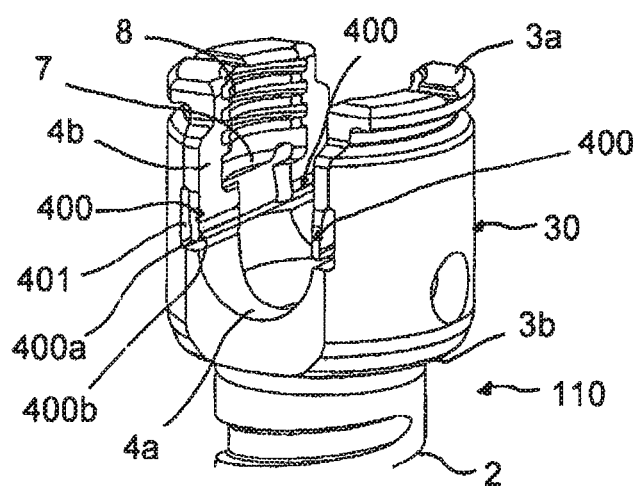
FIG. 11 shows a perspective view of a still further embodiment of a bone anchoring device in the form of a monoaxial bone anchoring device including a receiving part and a shank (shown only partially) connected thereto.
Figures 12A, 12B:
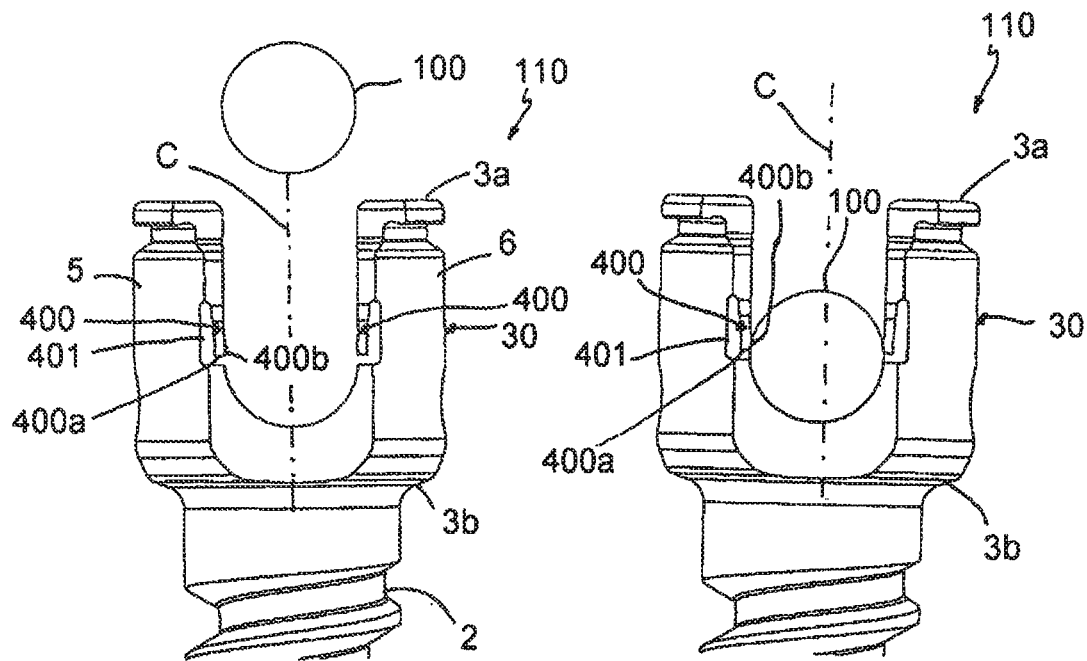
FIGS. 12a and 12b show front views of steps of inserting a rod into the bone anchoring device according to FIG. 11.
Figure 13:
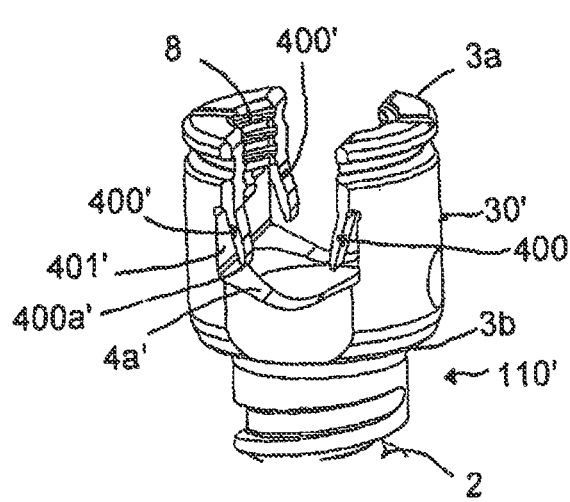
FIG. 13 shows a perspective view of a still further embodiment of a bone anchoring device in the form of a monoaxial bone anchoring device including a receiving part and a shank (shown only partially) connected thereto.
Figure 14:
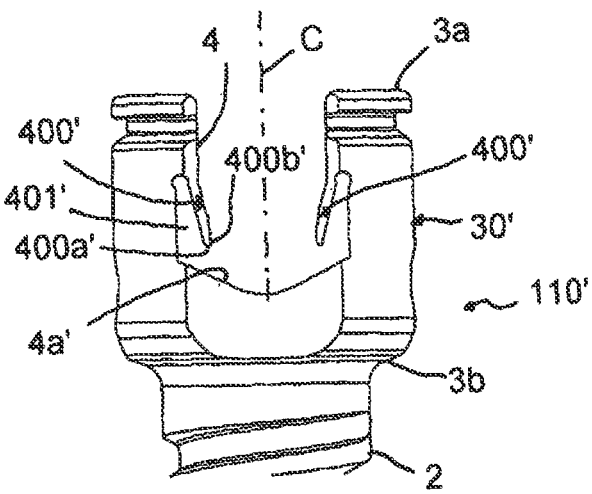
FIG. 14 shows a front view of the bone anchoring device of FIG. 13.

A further embodiment is shown in FIGS. 11, 12*a* and 12*b*. The bone anchoring device in this embodiment is shown as a monoaxial bone anchoring device 110 with a shank 2 rigidly connected to a receiving part 30. The receiving part 30 is similar to the receiving part 3 of FIGS. 1 to 3. Identical or similar parts and portions are indicated with the same reference numerals and the description thereof will not be repeated. The receiving part 30 differs from the previous embodiments in the design of the retention elements. The retention elements 400 each are shaped as resilient flaps having a free end 400*a* and are monolithically connected to the sidewall 4*b* at the end of the retention elements 400 opposite to the free end 400*a*. A recess or slit 401 provides space for deflection of the retention elements 400. The orientation of the flaps is such that the free end 400*a* is directed toward the second end 3*b* of the receiving part 30. As can be seen in FIG. 11, each recess 401 is open toward three sides. Adjacent to the free end 400*a*, an inner surface portion 400*b* of the retention elements 400 (i.e., a surface portion pointing toward the inside of the channel for the rod 100) is concavely shaped with a shape matching the shape of the rod 100. The retention elements 400 protrude into the channel such that when the rod 100 is not inserted in the receiving part 30, a shortest distance between respective retention elements 400 is smaller than the diameter of the rod 100 to be inserted.

In use, when the rod 100 is inserted, the rod 100 slides along the inner surface of the retention elements 400 and deflects the retention elements 400 outward and into the recesses 401. When the rod 100 is seated in the bottom 4*a* of the U-shaped recess 4, the rod 100 is clipped-in between the retention elements 400 and is provisionally and temporarily held there by the friction between the surface of the rod 100 and the concave surface portion 400*b* of the retention elements 400.

A modified embodiment is shown in FIGS. 13 to 16. The monoaxial bone anchoring device 110' of FIGS. 13 to 16 is configured to be used with at least two rods 100, 1000 having different diameters. The receiving part 30' differs from the receiving part 30 of FIGS. 11 to 12*b* in the shape of the retention elements and in the shape of the bottom of the recess forming the channel. The recess 4' forming the channel has a bottom 4*a*' that is not substantially circular. More specifically, the bottom 4*a*' is substantially V-shaped. The substantially V-shaped bottom 4*a*' allows placing rods 100, 1000 with different diameters in the channel, in particular cylindrical rods. When a cylindrical rod is used, the rod 100, 1000 has at least two lines of contact in a direction parallel to the longitudinal axis of the rod such that the rod is safely supported by the at least two lines of contact regardless of the diameter of the rod 100, 1000. The retention elements 400' are formed as flaps as in the previous embodiment. The flaps extend inward into the channel such that a cross-section of the recesses 401' is substantially triangular. A closed end portion 401*a*' of the recesses 401' may be enlarged and may have, for example, a cross-section that is a portion of a circle to facilitate bending of the flaps of the retention elements 400'. The inwardly protruding flaps reduce the width of the channel for the rod such that rods with a smaller diameter can be used and temporarily held. An inner surface of the retention elements 400' that faces toward the inside of the channel may have several concave surfaces portions 400*b*' at different positions to grip a corresponding rod 100, 1000.

Figure 15:
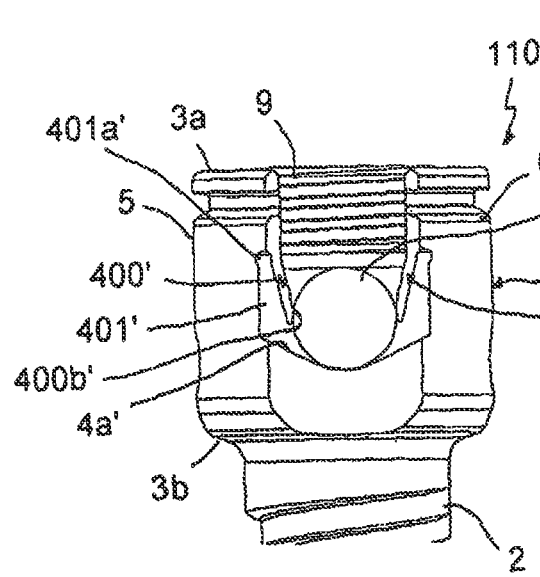
FIG. 15 shows a front view of the bone anchoring device of FIGS. 13 and 14 with a rod having a first diameter inserted therein and a fixation device.
Figure 16:
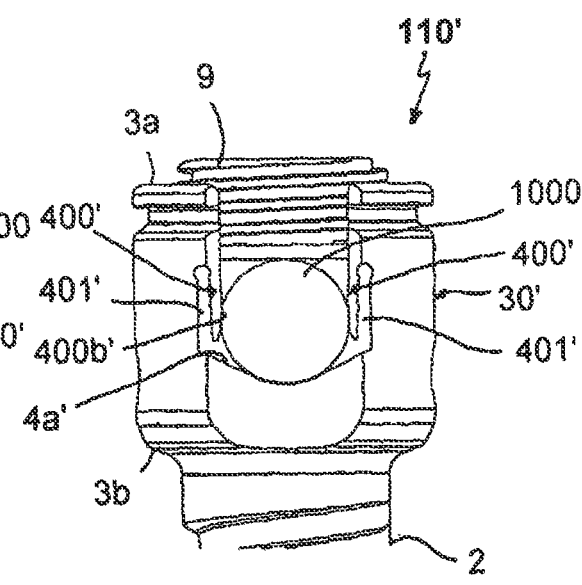
FIG. 16 shows a front view of the bone anchoring device of FIGS. 13 and 14 with a rod having a second diameter inserted therein and a fixation device.
Figure 17:
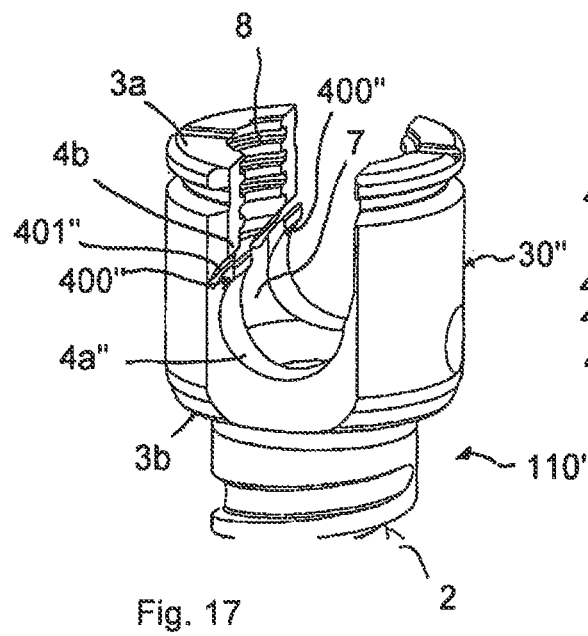
FIG. 17 shows a perspective view of a still further embodiment of a bone anchoring device including a receiving part and a shank (shown only partially) connected thereto.
Figure 18:
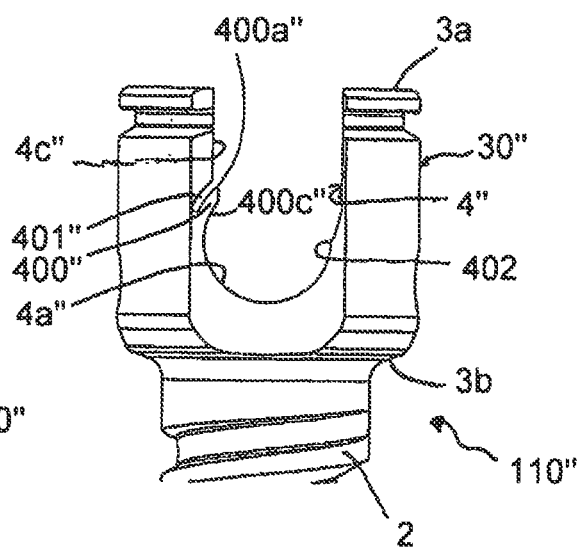
FIG. 18 shows a front view of the bone anchoring device of FIG. 17.

As depicted in FIG. 15, when a first rod 100 with a smaller diameter is used, for example a rod of a diameter of 4.5 mm, the retention elements 400' are only slightly deflected outward into the recesses 401'. As the rod 100 is supported along at least two contact lines in the bottom 4*a*' of the channel, the rod 100 is safely provisionally held by the retention elements 400' and the bottom 4*a*' of the channel. As illustrated in FIG. 16, when a rod 1000 with a larger diameter is used, for example a rod with a diameter of 5.5. mm, the rod 1000 deflects the retention elements 400 outward into the recesses 401' to a greater degree as compared to the smaller rod 100. Due to the resiliency of the retention elements 400', the angle of outward deflection when inserting the rod 100, 1000 can vary in a stepless manner. Hence, a variety of rods that differ in diameter can be temporarily held in the receiving part 30'.

A still further embodiment will be explained with reference to FIGS. 17 to 19*b*. The monoaxial bone anchoring device 110'' includes a shank 2 that is monoaxially connected to a receiving part 30''. The receiving part 30'' differs from the receiving part of the previous embodiments with respect to the arrangement of the recess for insertion of the rod and the retention elements. As in the previous embodiments, the receiving part 30" includes a bore 7 with a bore axis C that is coaxial with the shank axis. A recess 4" extends from the first end 3a of the receiving part 30" and ends in a bottom portion 4a" forming a rod seat that is located at a distance away from the second end 3b. The bottom portion 4a" has a substantially circular segment-shaped cross-section with a center of the circle lying in a plane that extends through the bore axis C. Furthermore, the recess 4" has an insertion portion 4c" with a substantially rectangular cross-section. The insertion portion 4c" extends into the bottom portion 4a" whereby a slightly protruding rib 402 is formed on one of each of the pairs of the opposing sidewalls 4b. The center plane of the insertion portion 4c" is offset from the bore axis C, as depicted in particular in FIGS. 19a and 19b. On each of the sidewalls 4b opposite to the protruding rib 402, a resilient retention element 400" is formed that has a free end 400a" facing the first end 3a of the receiving part 30'''. The resilient retention elements 400" have an inner contour 400c" facing the bore axis C that is substantially cylindrical and adapted to the size of the rod 100 to be received therein. Also, cylinderical segment-shaped recesses 401" provide space for outward deflection of the resilient retention element 400". Hence, in this embodiment, for each pair of opposing sidewalls 4b, there is one rigid retention element 402 in the form of a rib on one sidewall 4b and one resilient retention element 400" on an opposite sidewall 4b.

Figure 19A:
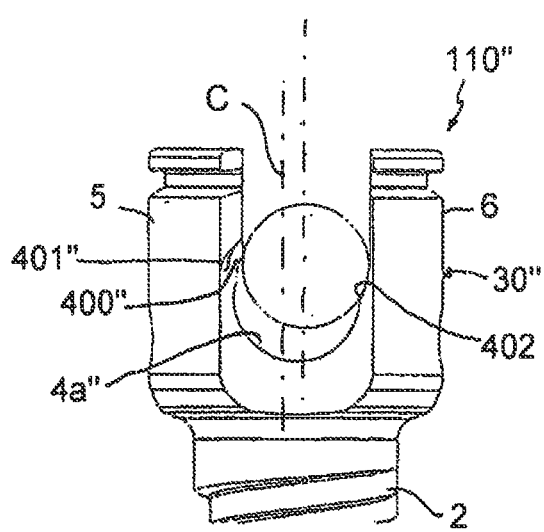
FIGS. 19a and 19b show front views of steps of inserting a rod into the bone anchoring device of FIGS. 17 and 18.
Figure 19B:
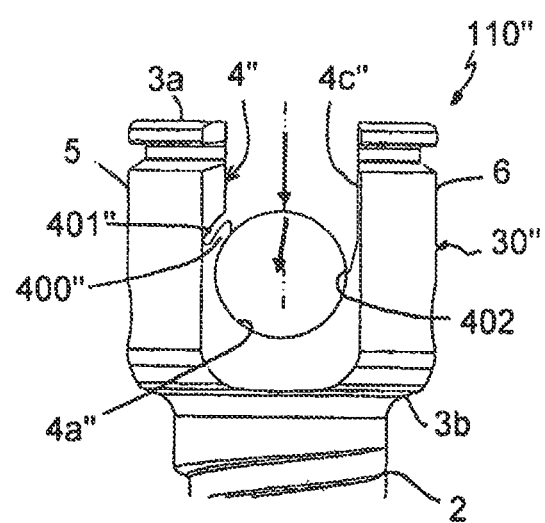
Figure 20:
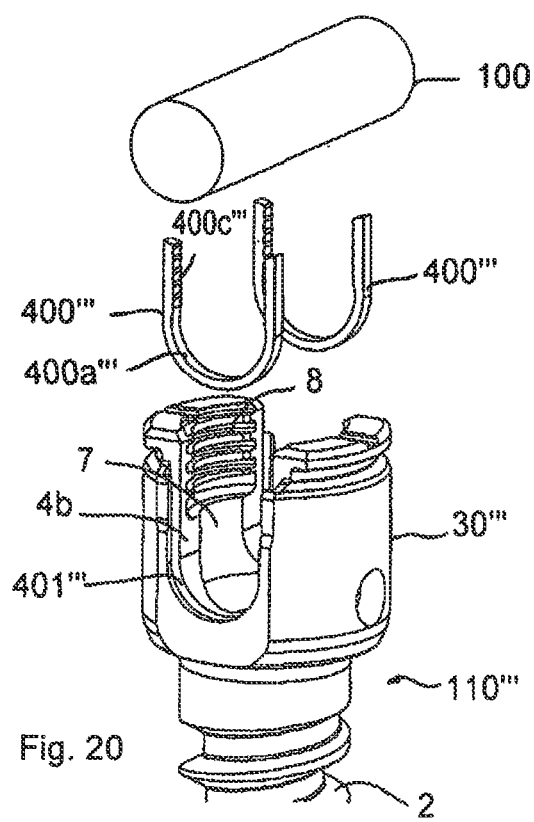
FIG. 20 shows a still further embodiment of a bone anchoring device in the form of a monoaxial bone anchoring device including a receiving part, a shank (shown only partially) connected thereto, separate retention elements, and a rod.
Figure 21:
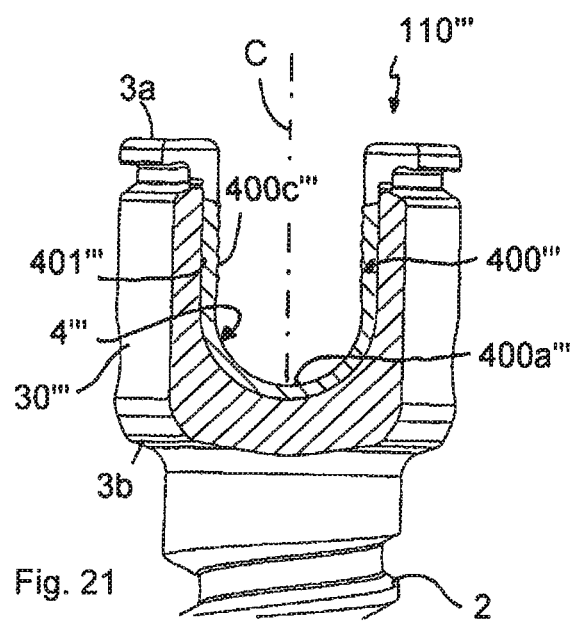
FIG. 21 shows a cross-sectional view of the bone anchoring device of FIG. 20 in an assembled state of the receiving part with the separate retention elements, the cross-section taken in a plane extending parallel to a bore axis of the receiving part and through a sidewall of the channel for the rod.
Figure 22A:
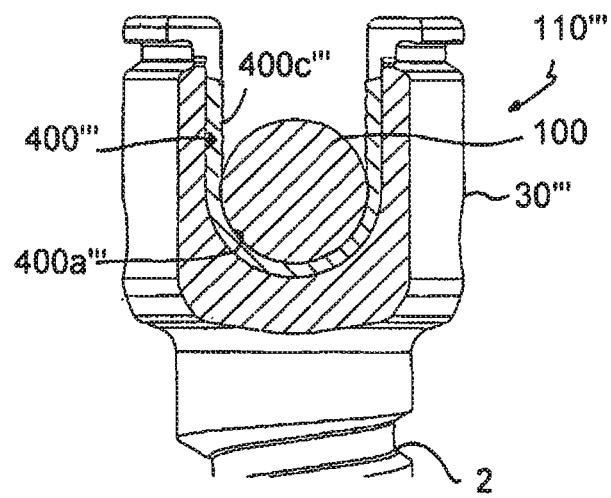
FIG. 22a shows a cross-sectional view of the bone anchoring device of FIG. 20 with the retention elements assembled as in FIG. 21 and with an inserted rod.
Figure 22B:
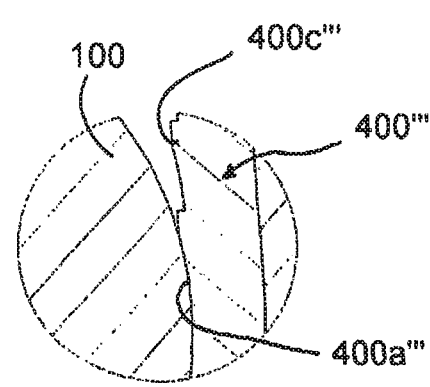

In use, as shown in FIG. 19a, when the rod 100 is inserted through the offset insertion portion 4c", the resilient retention element 400" is deflected outward until the rod 100 passes and snaps into the bottom portion 4a". The rod 100 is then temporarily held in the bottom portion 4a" by the retention elements 400", 402. Because the insertion portion 4c" is offset from a center of the bottom portion 4a", the free end 400a" of the retention elements 400" may be directed toward the insertion portion 4c" when the rod 100 is inserted without obstructing insertion of the rod 100. The gripping of the rod 100 may be enhanced thereby. It shall be noted that the rigid retention element 402 can also be omitted.

A still further embodiment will be explained with reference to FIGS. 20 to 22b. A monoaxial bone anchoring device 110''' according to this embodiment includes a shank 2 rigidly connected to a receiving part 30'''. The receiving part 30''' includes the bore 7 with the bore axis C being coaxial to the shank axis and a substantially U-shaped recess 4''' with a bottom 4''' for providing a rod seat. In this embodiment, the recess 4''' forming a channel for the rod 100 may be symmetrical to a plane extending through the bore axis C and containing the axis of the rod 100. Each of the sidewalls 4b formed by the substantially U-shaped recess 4''' includes a substantially U-shaped groove 401''' that serves for receiving a separate retention element 400'''. Each separate retention element 400''' is formed as a substantially U-shaped clip with an outer contour shaped to fit into the groove 401'''. The retention elements 400''' also include an inner contour that has a substantially cylinderical segment-shaped bottom portion 400a''' serving as a rod seat and a gripping contour 400c''' between the bottom portion 400a''' and the free ends of the retention element 400". The gripping contour 400c''' may have, for example, a teeth-like structure with teeth facing upward toward the first end 3a of the receiving part 30'''. The gripping contour 400c''' serves for slightly clamping the rod 100 in the channel when the rod 100 is inserted therein. In the embodiment shown, the separate retention elements 400''' are provided on either side of the bore 7. The retention elements 400''' may be designed such that when the rod 100 is inserted into the receiving part 30''', the arms of the retention elements 400''' are slightly bent outward toward the groove 401''' and are thereby clamped in the groove 401'''. The material of the retention elements 400''' may be a material that has a greater elasticity than a retention element made of the same material as the receiving part 30'''. For example, the separate retention elements 400''' may be made from a super-elastic body-compatible metal alloy or from a body-compatible plastic material.

In use, when the rod 100 is inserted into the receiving part 30''', the rod 100 presses the arms of the separate retention element 400''' outward so that the retention elements 400''' become clamped in the grooves 401'''. The rod 100 is then held in the bottom portion 400a''' by the gripping contours 400c''' of the retention elements 400'''.

It shall be understood that each of the embodiments described can also be realized in the receiving part of a polyaxial bone anchoring device, as depicted in FIGS. 5 to 10.

Figure 23:
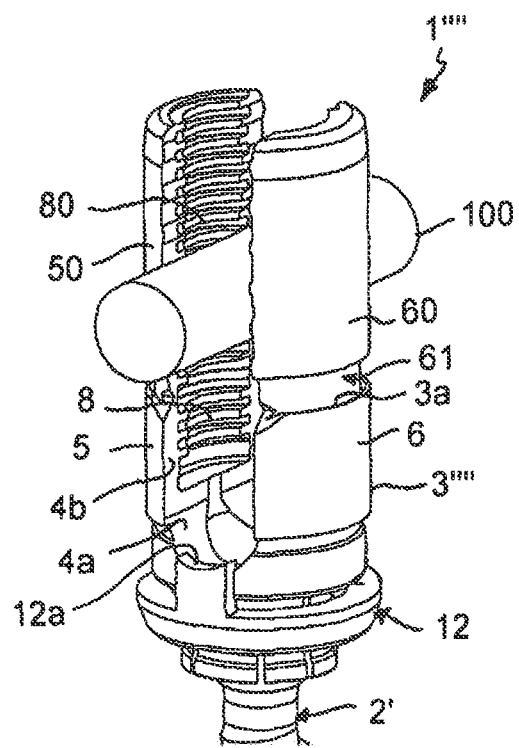
FIG. 23 shows a further embodiment of a bone anchoring device including a receiving part having break-off extension tabs, a bone anchor that is polyaxially connectable to the receiving part and that can be locked by an outer ring, and a rod.
Figure 24A:
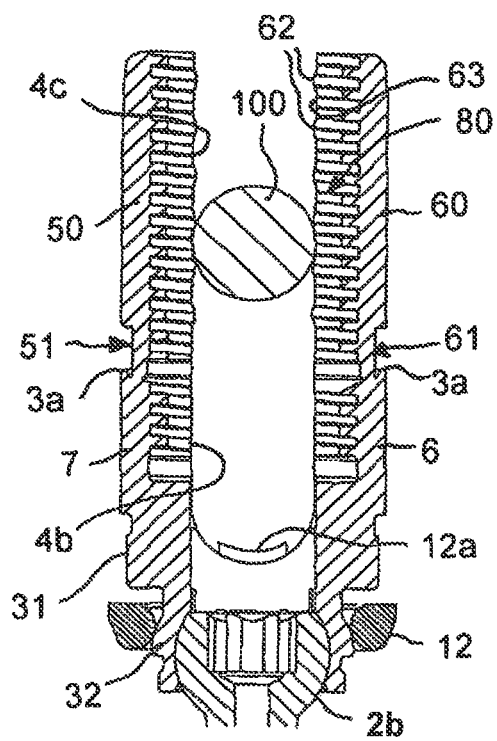
FIG. 24a shows a cross-sectional view of the bone anchoring device of FIG. 23, the-cross section taken in a plane extending parallel to a bore axis of the receiving part and through a sidewall of the channel for the rod.
Figure 24B:
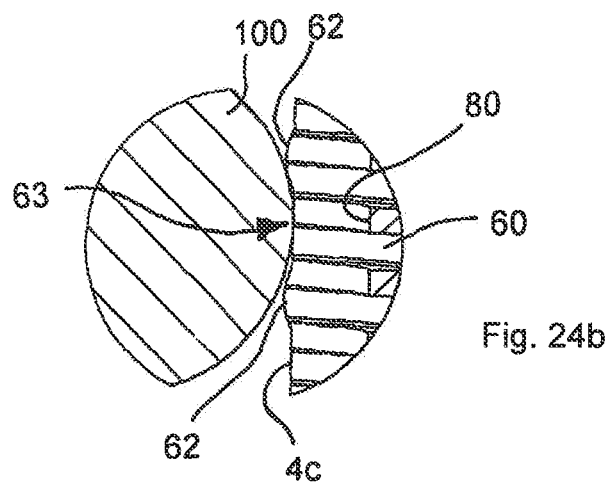

A further embodiment of a bone anchoring device 1'''' is shown in FIGS. 23 through 24b. The bone anchoring device 1'''' of FIGS. 23 to 24b is similar to the bone anchoring device 1''' shown in FIGS. 9 and 10, and is formed as a bottom-loading polyaxial bone anchoring device, where the head 2b of the bone anchor 2' is clamped by an outer locking ring 12. Only those parts differing from the embodiment of FIGS. 9 and 10 will be explained in the following, while a detailed description of identical or similar features is not repeated herein.

The receiving part 3'''' has a rod-receiving portion 31 that includes the recess 4 forming the channel for receiving the rod 100. Moreover, the rod-receiving portion 31 has two legs 5, 6 separated from each other by the recess 4. The two legs 5, 6 include the first end 3a of the receiving part 3'''' at respective upper tips of the receiving part 3''''. However, before removal thereof, break-off extension tabs 50, 60 monolithically extend from the first end 3a at each of the legs 5, 6, respectively. The use of break-off extension tabs is generally well known in the art. The break-off extension tabs 50, 60 of this embodiment, among other features, help in guiding an inserted rod 100 towards the rod-receiving portion 31 of the receiving part 3''''. Once the rod 100 has been guided through the inner sidewalls 4c of the break-off extension tabs 50, 60 and a fixation element 9 (not shown in FIGS. 23 to 24b) has been threaded through an inner thread 80 of the break-off extension tabs 50, 60, the break-off extension tabs 50, 60 may be removed by bending them away around predetermined breaking points 51, 61. The predetermined breaking points 51, 61 are formed as thinned wall portions of the receiving part 3'''' at the first end 3a. In this embodiment, the predetermined breaking points 51, 61 are formed as circumferential grooves or cutouts in an outer wall surface of the receiving part 3''''.

Due to the predetermined breaking points 51, 61, the break-off extension tabs 50, 60 are resiliently bendable prior to undergoing a bending force sufficient to break-off the extension tabs 50, 60. Further, the opposed inner sidewalls 4c of the break-off extension tabs 50, 60 are separated by a distance that is the same as the distance between the opposed sidewalls 4b of the legs 5, 6 to allow the rod 100 to be guided therethrough to a position in which the rod 100 rests on the projections 12a of the retaining ring 12. However, one or more retention projections 62 may be formed on each of the opposed sidewalls 4c, which narrow the width of the recess 4 between the inner sidewalls 4c in this upper portion. Due to the resiliency of the tabs 50, 60, the rod 100 may, upon insertion, be temporarily held in a flat portion 63 of the sidewalls 4c between two retention projections 62. Also, the tabs 50, 60 bend away from each other when the rod 100 passes opposed retention projections 62 urging the opposed retention projections 62 outwards.

It may be noted that the retention projections 62 may be provided on just one of the two sidewalls 4c. Moreover, the retention projections 62 may form a regular pattern, where, for example, 4 to 6 retention projections 62 are formed on each sidewall 4c, such that a ratchet-like holding mechanism may be established for the rod 100. Such a configuration may give a tactile response to the operator of the bone anchoring device 1''" and further allows the rod 100 to be held at a number of possible vertical positions above the rod-receiving portion 31 according to an operator's specific needs. As the upper ends of the break-off extension tabs 50, 60 move further away from each other at given bending force as compared with portions of the tabs 50, 60 closer to the breakage points 51, 61, the holding force for temporarily holding the rod 100 increases at retention projections 62 positioned closer to the rod-receiving portion 31 (towards the bottom end) allowing the operator to select a temporary holding force for the rod 100 as desired. In this embodiment, the bendable break-off extensions tabs 50, 60, including the retention projections 62, form resilient retention elements.

Further modifications of the embodiments described are possible. The retention elements are not restricted to the specific shapes shown in the embodiments. Deviations therefrom are possible as long as the same function is achieved.

Although the embodiments describe bone anchoring devices where the rod is loaded into the receiving part from a top side of the receiving part, the invention can also be realized in a side-loading device where the rod is insertable into the receiving part from the side, i.e., the insertion direction of the rod includes an angle, for example 90°, with respect to the bore axis.

For the fixation device, all types of known fixation devices can be used, such as dual-part fixation devices, outer nuts, bayonet fixation devices, and others.

For the bone anchor, all types of bone anchors can be used, such as a screw-type bone anchor having a threaded shank, a nail-type bone anchor with or without barbs, a cannulated bone anchor, hooks, and others.

Although the example rods shown in the embodiments are cylindrical rods, the rods do not necessarily need to be cylindrical, but can have another cross-sectional shape such as rectangular, square-shaped, oval-shaped and others. The cross-sectional shape of the rods do not need to be constant over the whole length of the rods. The rods may be smooth or may be roughened or otherwise structured. Also, multi-piece and curved rods may be contemplated.

A number of different embodiments are disclosed herein. It is appreciated that the components of the different embodiments can be mixed and matched to produce other different embodiments.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A bone anchoring device connectable to a bone anchor that comprises a shank for anchoring to a bone or a vertebra, the bone anchoring device comprising:
   a rod; and
   a receiving part comprising:
      a first end, a second end below the first end, and a central axis extending between the first and second ends;
      a bore extending coaxially from the first end into the receiving part for receiving a fixation device from the first end to lock the rod;
      a recess for receiving the rod, the recess being open at the first end of the receiving part and extending down toward the second end to form two legs on the receiving part, wherein a longitudinal axis of the recess extends substantially perpendicular to the central axis, such that the recess extends through a first side of the receiving part and forms opposing sidewalls on the two legs that face one another at the first side, and further extends through an opposite second side of the receiving part; and
      a retention element provided at at least a first sidewall of the opposing sidewalls, wherein the retention element extends axially to a free end that is spaced apart from the first sidewall in a direction transverse to the central axis, and wherein the free end of the retention element is deflectable away from the longitudinal axis of the recess towards the first sidewall;
   wherein when the rod is at a lowermost axial position in the recess, the retention element is configured to contact a portion of the rod that is below a region of the rod that defines a greatest diameter of the rod measured in a direction perpendicular to the central axis.

2. The bone anchoring device of claim 1, wherein the retention element is configured to extend into the recess to an extent such that the retention element can frictionally hold the rod when the rod is in the recess.

3. The bone anchoring device of claim 1, wherein a second set of opposing sidewalls that face one another is provided at the opposite second side of the receiving part, and wherein a retention element is provided at at least one sidewall of the second set of opposing sidewalls.

4. The bone anchoring device of claim 1, wherein the free end of the retention element is spaced apart from the first sidewall by a slit.

5. The bone anchoring device of claim 4, wherein the slit opens axially into the recess adjacent the free end of the retention element.

6. The bone anchoring device of claim 1, wherein the retention element is monolithically formed with other portions of the receiving part.

7. The bone anchoring device of claim 1, wherein a bottom of the recess has a shape that is configured to interchangeably support at least two rods having different diameters, and wherein the retention element is also configured to engage rods of different diameters.

8. The bone anchoring device of claim 1, wherein the retention element provided at at least the first sidewall of the opposing sidewalls comprises two retention elements respectively provided at both of the opposing sidewalls.

9. The bone anchoring device of claim 1, wherein an end of the retention element opposite the free end is connected to the first sidewall.

10. The bone anchoring device of claim 1, wherein the retention element extends away from the first end of the receiving part, such that the free end of the retention element is positioned farther away from the first end than other portions of the retention element are from the first end.

11. A receiving part for coupling a bone anchor to a rod, the bone anchor comprising a shank for anchoring to a bone or a vertebra, the receiving part comprising:

a first end, a second end, and a central axis extending between the first and second ends;

a bore extending coaxially from the first end into the receiving part for receiving a fixation device from the first end to lock the rod;

a recess for receiving the rod, the recess being open at the first end of the receiving part and extending toward the second end to form two legs on the receiving part, wherein the central axis extends through at least part of the recess and a longitudinal axis of the recess extends substantially perpendicular to the central axis, such that the recess extends through a first side of the receiving part and forms opposing sidewalls on the two legs that face one another at the first side, and further extends through an opposite second side of the receiving part; and a retention element provided at at least a first sidewall of the opposing sidewalls, wherein the retention element is deflectable when the rod is received in the recess;

wherein the recess has an insertion portion for inserting the rod and a rod seat portion for holding the rod, the insertion portion and the rod seat portion each having a central plane that extends in a direction of the longitudinal axis of the recess, and wherein the central plane of the insertion portion and the central plane of the rod seat portion are offset from one another in a direction transverse to the central axis of the receiving part.

12. The receiving part of claim 11, wherein a second set of opposing sidewalls that face one another is provided at the opposite second side of the receiving part, and wherein a retention element is provided at at least one sidewall of the second set of opposing sidewalls.

13. The receiving part of claim 11, wherein the retention element extends axially to a free end that is spaced apart from the first sidewall in the direction transverse to the central axis.

14. The receiving part of claim 13, wherein the retention element extends towards the first end of the receiving part, such that the free end of the retention element is positioned closer to the first end than other portions of the retention element are to the first end.

15. The receiving part of claim 11, wherein the central plane of the rod seat portion includes the longitudinal axis of the recess and the central axis of the receiving part, while the central plane of the insertion portion is spaced apart laterally from the central axis of the receiving part.

16. The receiving part of claim 11, wherein the retention element is provided at or near a transition between the insertion portion and the rod seat portion of the recess.

17. The receiving part of claim 11, wherein a further retention element is not provided at a corresponding sidewall opposite the first sidewall.

18. The receiving part of claim 11, wherein the retention element is monolithically formed with other portions of the receiving part.

19. A bone anchoring device comprising the receiving part according to claim 11 and the rod, wherein the retention element is configured to extend into the recess to an extent such that the retention element can frictionally hold the rod when the rod is in the recess.

20. The receiving part of claim 11, wherein the two legs are formed on opposite sides of the central axis in the direction transverse to the longitudinal axis.

* * * * *

UNITED STATES PATENT AND TRADEMARK OFFICE
CERTIFICATE OF CORRECTION

PATENT NO. : 11,197,693 B2
APPLICATION NO. : 16/796336
DATED : December 14, 2021
INVENTOR(S) : Lutz Biedermann et al.

It is certified that error appears in the above-identified patent and that said Letters Patent is hereby corrected as shown below:

In the Specification

Column 9, Line 47        Delete "4'''" and
                         insert -- 4a''' --

Column 9, Line 60        Delete "400"." and
                         insert -- 400'''. --

Signed and Sealed this
Tenth Day of January, 2023

*Katherine Kelly Vidal*

Katherine Kelly Vidal
*Director of the United States Patent and Trademark Office*